United States Patent [19]

Krämer et al.

[11] Patent Number: 5,177,103
[45] Date of Patent: Jan. 5, 1993

[54] PESTICIDAL AMINOMETHYLHETEROCYCLIC COMPOUNDS

[75] Inventors: Wolfgang Krämer, Burscheid; Joachim Weissmüller, Monheim; Dieter Berg, Wuppertal; Wilhelm Brandes, Leichlingen; Stefan Dutzmann, Duesseldorf, all of Fed. Rep. of Germany

[73] Assignee: Bayer Aktiengesellschaft, Leverkusen, Fed. Rep. of Germany

[21] Appl. No.: 616,155

[22] Filed: Nov. 20, 1990

Related U.S. Application Data

[62] Division of Ser. No. 395,391, Aug. 17, 1989, Pat. No. 5,010,101.

[30] Foreign Application Priority Data

Aug. 23, 1988 [DE] Fed. Rep. of Germany ....... 3828545

[51] Int. Cl.$^5$ .................... A01N 43/28; C07D 327/04
[52] U.S. Cl. ........................................ 514/439; 549/30
[58] Field of Search ............................. 549/30; 514/439

[56] References Cited

U.S. PATENT DOCUMENTS 4,851,405  7/1989  Kramer et al. ..................... 514/212

FOREIGN PATENT DOCUMENTS

| | | |
|---|---|---|
| 0097822 | 1/1984 | European Pat. Off. . |
| 0131793 | 1/1985 | European Pat. Off. . |
| 0281842 | 9/1988 | European Pat. Off. . |
| 0349247 | 1/1990 | European Pat. Off. . |
| 1965321 | 8/1970 | Fed. Rep. of Germany . |

OTHER PUBLICATIONS

Chemical and Pharmaceutical Bulletin, vol. 32, No. 3 (1984), pp. 967–976, "Studies on ... -4-ylmethyl)piperidines".
Kramer et al. II, "Oxaspirodecanes-containing, etc." CA 111:19467q (1989).

*Primary Examiner*—Patricia L. Morris
*Attorney, Agent, or Firm*—Sprung Horn Kramer & Woods

[57] ABSTRACT

Fungicidally active compounds of the formula

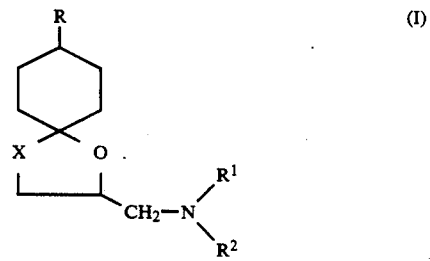

in which
X represents oxygen or sulphur,
R represents cycloalkyl, or represents optionally substituted aryl, or represents the radical

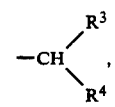

$R^1$ and $R^2$ each independently is hydrogen or an organic radical, or together with the nitrogen atom form a heterocyclic radical,
$R^3$ represents hydrogen, alkyl or optionally substituted aryl, and
$R^4$ represents alkyl or cycloalkyl, or represents optionally substituted aryl,
but wherein $R^3$ and $R^4$ may not simultaneously represent methyl,
and acid addition salts thereof, as well as intermediates therefor.

5 Claims, No Drawings

PESTICIDAL AMINOMETHYLHETEROCYCLIC COMPOUNDS

This is a division of application Ser. No. 395,391, filed Aug. 17, 1989, now U.S. Pat. No. 5,010,101.

The invention relates to new aminomethylheterocyclic compounds, several processes for their preparation, their use in agents for combating pests and new intermediate products.

It is known that certain aminomethyldioxolanes, such as, for example, the compound 2-isobutyl-2-methyl-4-(1-piperidinylmethyl)-1,3-dioxolane or the compound 2-methyl-2-nonyl-4-di-n-butylaminomethyl-1,3-dioxolane or the compound 2-(2-cyclohexylmethyl-2-propyl)-2-methyl-4-(1-piperidinylmethyl)-1,3-dioxolane or the compound 2-(2-cyclohexylmethyl-2-propyl)-2-methyl-4-(1-perhydroazepinylmethyl)-1,3-dioxolane, have fungicidal properties (compare, for example, EP 97,822).

However, the activity of these already known compounds is not completely satisfactory in all fields of use, especially when low amounts are applied and in the case of low concentrations.

New aminomethylheterocyclic compounds of the general formula (I)

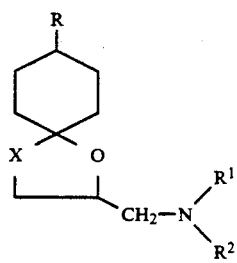

(I)

in which
X represents oxygen or sulphur,
R represents cycloalkyl, or represents optionally substituted aryl, or represents a radical

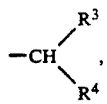

, $R^1$ and $R^2$ independently of one another each represent hydrogen, alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl, or represent in each case optionally substituted cycloalkylalkyl, cycloalkyl, aralkyl, aralkenyl or aryl, or $R^1$ and $R^2$, together with the nitrogen atom to which they are bonded, represent an optionally substituted saturated heterocyclic radical, which can optionally contain further hetero atoms, and $R^3$ represents hydrogen, alkyl or optionally substituted aryl and $R^4$ represents alkyl or cycloalkyl, or represents optionally substituted aryl, but wherein $R^3$ and $R^4$ may not simultaneously represent methyl, and acid addition salts thereof, have been found.

The compounds of the formula (I) can exist as geometric and/or optical isomers or isomer mixtures of varying composition. Both the pure isomers and the isomer mixtures are claimed according to the invention when compounds of the formula (I) are referred to.

It has furthermore been found that the new aminomethylheterocyclic compounds of the general formula (I)

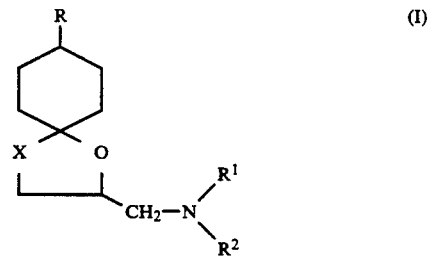

(I)

in which
X represents oxygen or sulphur,
R represents cycloalkyl, or represents optionally substituted aryl, or represents a radical

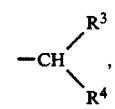

, $R^3$ represents hydrogen, alkyl or optionally substituted aryl and $R^4$ represents alkyl or cycloalkyl, or represents optionally substituted aryl, but wherein $R^3$ and $R^4$ may not simultaneously represent methyl, $R^1$ and $R^2$ independently of one another each represent hydrogen, alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl, or represent in each case optionally substituted cycloalkylalkyl, cycloalkyl, aralkyl, aralkenyl or aryl, or $R^1$ and $R^2$, together with the nitrogen atom to which they are bonded, represent an optionally substituted saturated heterocyclic radical, which can optionally contain further hetero atoms, and acid addition salts thereof, are obtained by a process in which (a) substituted heterocyclic compounds of the formula (II)

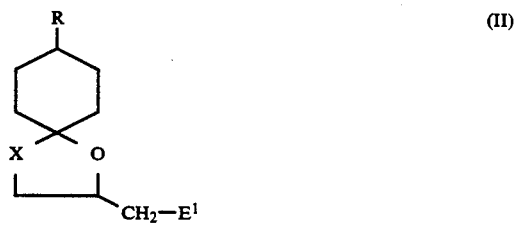

(II)

in which
R and X have the abovementioned meanings and
$E^1$ represents an electron-withdrawing leaving group,
are reacted with amines of the formula (III)

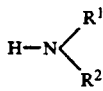

(III)

in which

R$^1$ and R$^2$ have the abovementioned meanings,
if appropriate in the presence of a diluent and if appropriate in the presence of an acid-binding agent, or by a process in which (b) the aminomethylheterocyclic compounds obtainable by process (a), of the formula (Ia)

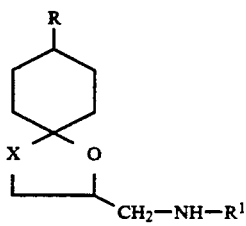

(Ia)

in which

R, R$^1$ and X have the abovementioned meanings,
are reacted with alkylating agents of the formula (IV)

$$R^{2\text{-}1}\text{—}E^2 \qquad (IV)$$

in which

R$^{2\text{-}1}$ represents alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl, or represents in each case optionally substituted cycloalkylalkyl, cycloalkyl, aralkyl or aralkenyl and E$^2$ represents an electron-withdrawing leaving group,
if appropriate in the presence of a diluent and if appropriate in the presence of an acid-binding agent, and, if appropriate, an acid is then added on or the reaction is followed by a physical resolution method.

Finally, it has been found that the new aminomethylheterocyclic compounds of the general formula (I) have an action against pests, in particular against fungal pests.

Surprisingly, the aminomethylheterocyclic compounds of the general formula (I) according to the invention inter alia exhibit a better fungicidal activity than the aminomethyldioxolanes known from the prior art, such as, for example, the compound 2-isobutyl-2-methyl-4-(1-piperidinylmethyl)-1,3-dioxolane or the compound 2-methyl-2-nonyl-4-di-n-butylaminomethyl-1,3-dioxolane or the compound 2-(2-cyclohexylmethyl-2-propyl)-2-methyl-4-(1-piperidinylmethyl)-1,3-dioxolane or the compound 2-(2-cyclohexylmethyl-2-propyl)2-methyl-4-(1-perhydroazepinylmethyl)-1,3-dioxolane, which are closely related compounds chemically and from the point of view of their action.

Formula (I) provides a general definition of the aminomethylheterocyclic compounds according to the invention. Preferred compounds of the formula (I) are those in which X represents oxygen or sulphur, R represents cycloalkyl having 3 to 7 carbon atoms, or represents aryl which has 6 to 10 carbon atoms and is optionally substituted by one or more identical or different straight-chain or branched alkyl radicals having 1 to 12 carbon atoms, or represents a radical $$-CH\begin{matrix}R^3\\R^4\end{matrix},$$

R$^1$ and R$^2$ independently of one another each represent hydrogen, or represent in each case straight-chain or branched alkyl having 1 to 12 carbon atoms, alkenyl having 3 to 8 carbon atoms, alkinyl having 3 to 8 carbon atoms, hydroxyalkyl having 2 to 6 carbon atoms, alkoxyalkyl or dialkoxyalkyl having in each case 1 to 6 carbon atoms or hydroxyalkoxyalkyl having 2 to 6 carbon atoms in the individual alkyl parts, or represent alkoxycarbonylalkyl having 1 to 6 carbon atoms per alkoxy and alkyl part, or represent in each case straight-chain or branched dioxolanylalkyl, dioxanylalkyl or oxolanylalkyl having in each case 1 to 4 carbon atoms in the alkyl part, or represent cycloalkyl or cycloalkylalkyl having in each case 3 to 7 carbon atoms in the cycloalkyl part and if appropriate 1 to 4 carbon atoms in the straight-chain or branched alkyl part and in each case optionally substituted in the cycloalkyl part by one or more identical or different substituents, possible substituents in each case being: halogen and in each case straight-chain or branched alkyl, alkoxy, halogenoalkyl and halogenoalkoxy having in each case 1 to 4 carbon atoms and if appropriate 1 to 9 identical or different halogen atoms;

or in addition represent arylalkyl, arylalkenyl or aryl having in each case 6 to 10 carbon atoms in the aryl part and if appropriate up to 6 carbon atoms in the straight-chain or branched alkyl or alkenyl part and in each case optionally substituted in the aryl part by one or more identical or different substituents, possible substituents on the aryl in each case being:

halogen, cyano, nitro and in each case straight-chain or branched alkyl, alkoxy, alkylthio, halogenoalkyl, halogenoalkoxy, halogenoalkylthio, alkoxycarbonyl and alkoximinoalkyl having in each case 1 to 4 carbon atoms in the individual alkyl parts and if appropriate 1 to 9 identical or different halogen atoms, or R$^1$ and R$^2$, together with the nitrogen atom to which they are bonded, represent a saturated 5- to 7-membered heterocyclic radical which is optionally substituted by one or more identical or different substituents and can optionally contain a further hetero atom, in particular nitrogen, oxygen or sulphur, possible substituents being: in each case straight-chain or branched alkyl or hydroxyalkyl having in each case 1 to 4 carbon atoms, R$^3$ represents hydrogen, or represents straight-chain or branched alkyl having 1 to 12 carbon atoms, or represents aryl which has 6 to 10 carbon atoms and is optionally substituted by one or more identical or different straight-chain or branched alkyl radicals having 1 to 12 carbon atoms and R$^4$ represents straight-chain or branched alkyl having 1 to 12 carbon atoms, or represents cycloalkyl having 3 to 7 carbon atoms, or represents aryl which has 6 to 10 carbon atoms and is optionally substituted by one or more identical or different straight-chain or branched alkyl radicals having 1 to 12 carbon atoms, but wherein R$^3$ and R$^4$ may not simultaneously represent methyl.

Particularly preferred compounds of the formula (I) are those in which

X represents oxygen or sulphur

R represents cyclopentyl or cyclohexyl, or represents phenyl which is optionally substituted by one to three identical or different substituents from the group comprising methyl, ethyl, n- or i-propyl and n-, i-, s- or t-butyl, or represents a radical

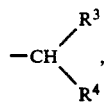

R$^1$ and R$^2$ independently of one another each represent hydrogen methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, dioxanylethyl, oxolanylmethyl or oxolanylethyl, or represent cyclopropyl, cyclopropylmethyl, cyclopropylethyl, cyclopropylpropyl, cyclopentyl, cyclopentylmethyl, cyclohexyl or cyclohexylmethyl, in each case, optionally substituted by one to five identical or different substituents from the group comprising fluorine, chlorine, bromine, methyl, ethyl, n- or i-propyl, n-, i-, s- or t-butyl, trifluoromethyl and trifluoromethoxy, or represent phenyl, benzyl or phenethyl, in each case optionally substituted by one to three identical or different substituents, possible substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl or methoximinomethyl, or R$^1$ and R$^2$, together with the nitrogen atom to which they are bonded, represent a heterocyclic radical of the formula

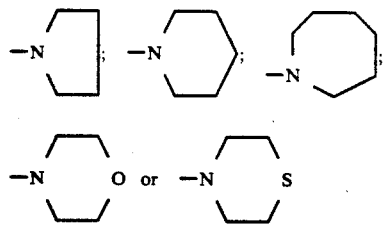

which is optionally substituted by one to three identical or different substituents, possible substituents in each case being: methyl, ethyl and hydroxymethyl, and R$^3$ represents hydrogen, methyl, ethyl or n- or i-propyl, or represents in each case straight-chain or branched butyl, pentyl or hexyl, or represents phenyl which is optionally substituted by one to three identical or different substituents from the group comprising methyl, ethyl, n- or i-propyl and n-, i-, s- or t-butyl and R$^4$ represents methyl, ethyl or n- or i-propyl, or represents in each case straight-chain or branched butyl, pentyl or hexyl, or represents cyclopentyl or cyclohexyl, or represents phenyl which is optionally substituted by one to three identical or different substituents from the group comprising methyl, ethyl, n-or i-propyl and n-, i-, s- or t-butyl, but wherein R$^3$ and R$^4$ may not simultaneously represent methyl.

Especially preferred compounds of the formula (I) are those in which

X represents oxygen or sulphur,

R represents cyclohexyl, or represents phenyl, or represents a radical

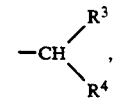

R$^1$ and R$^2$ independently of one another each represent hydrogen, methyl, ethyl, n- or i-propyl, n-, i-, s-or t-butyl, n- or i-pentyl, n- or i-hexyl, allyl, n-or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, oxolanylmethyl, oxolanylethyl, cyclopropylmethyl, dichlorocyclopropylmethyl, dimethylcyclopropylmethyl, dichlorodimethylcyclopropylmethyl, cyclopentyl, cyclhexyl or cyclohexylmethyl, or R$^1$ and R$^2$, together with the nitrogen atom to which they are bonded, represent a heterocyclic radical of the formula

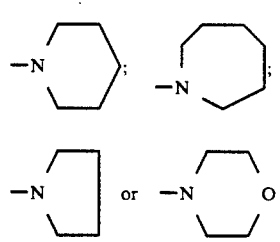

which is optionally substituted by one to three identical or different substituents, possible substituents in each case being: methyl, ethyl and hydroxymethyl, and R$^3$ represents hydrogen, methyl, ethyl, n- or i-propyl, n-, i-, s- or t-butyl or phenyl and R$^4$ represents methyl, ethyl, n- or i-propyl, n-, i-, s- or t-butyl, or represents cyclohexyl, or represents phenyl, but wherein R$^3$ and R$^4$ may not simultaneously represent methyl.

Addition products of acids and those aminomethylheterocyclic compounds of the formula (I) in which the substituents X, R, R$^1$ and R$^2$ have the meanings which have already been mentioned for these substituents are also preferred compounds according to the invention.

The acids which can be added on include, preferably hydrogen halide acids, such as, for example, hydrochloric acid and hydrobromic acid, in particular hydrochloric acid, and furthermore phosphoric acid, nitric acid, mono-, bi- and trifunctional carboxylic acids and hydroxycarboxylic acids, such as, for example, acetic acid, maleic acid, succinic acid, fumaric acid, tartaric acid,

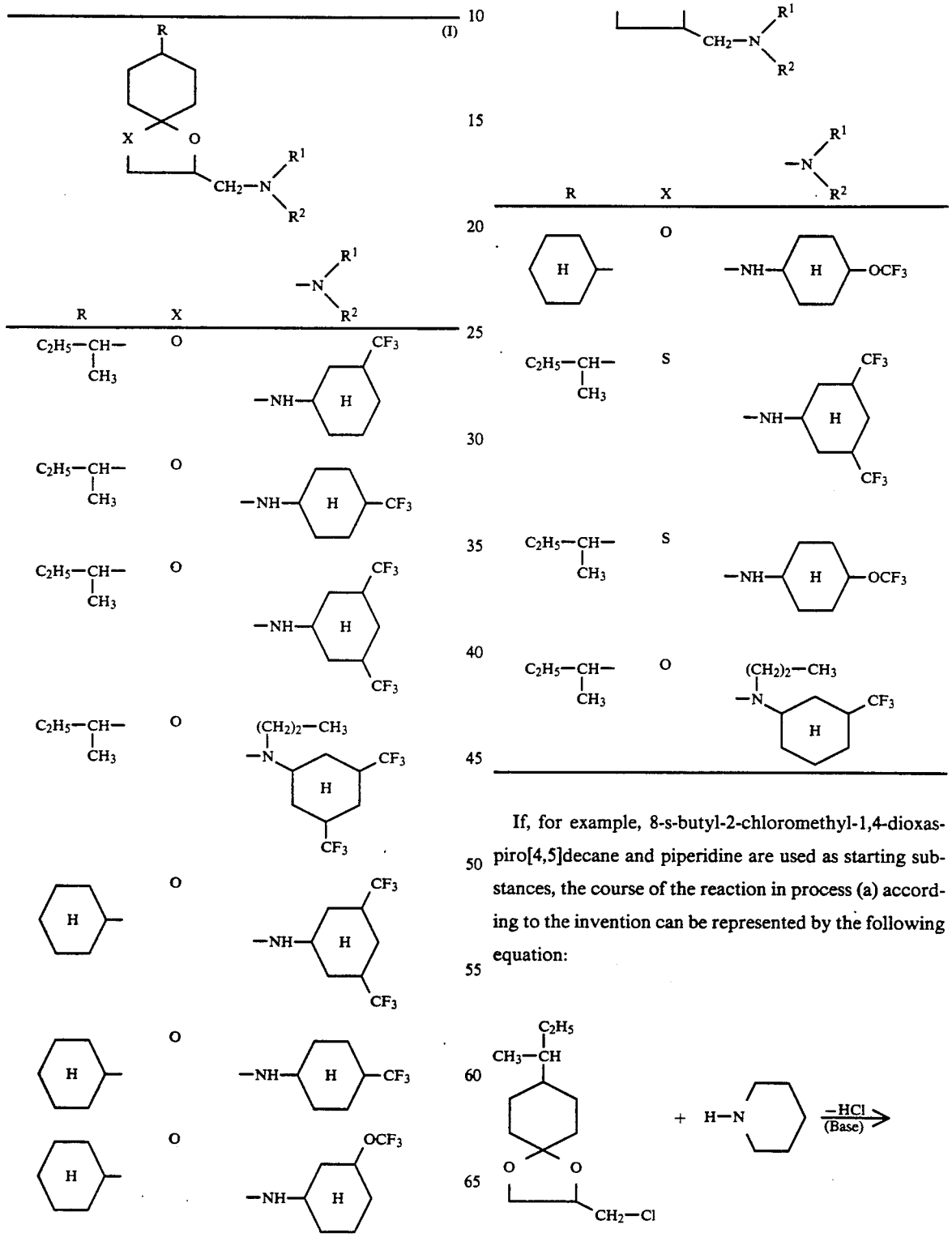

citric acid, salicylic acid, sorbic acid and lactic acid, and sulphonic acids, such as p-toluenesulphonic acid and 1,5-naphthalenedisulphonic acid, and furthermore saccharin.

The following aminomethylheterocyclic compounds of the general formula (I) may be mentioned specifically, in addition to the compounds mentioned in the preparation examples:

If, for example, 8-s-butyl-2-chloromethyl-1,4-dioxaspiro[4,5]decane and piperidine are used as starting substances, the course of the reaction in process (a) according to the invention can be represented by the following equation:

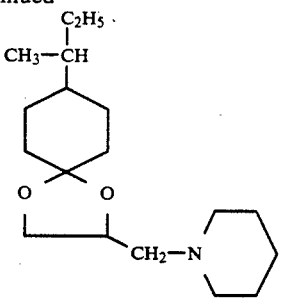

If, for example, 8-cyclohexyl-2-methylaminomethyl-1,4-dioxaspiro[4,5]decane and allyl bromide are used as starting substances, the course of the reaction in process (b) according to the invention can be represented by the following equation:

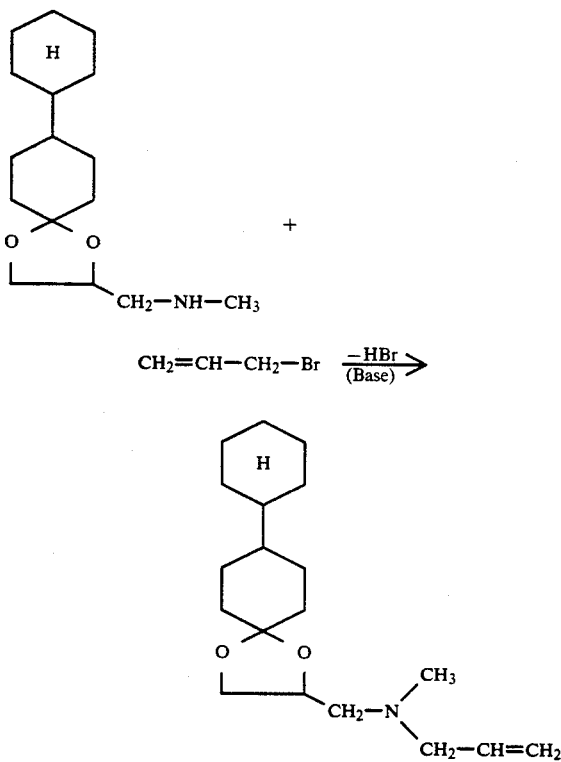

Formula (II) provides a general definition of the substituted heterocyclic compounds required as starting substances for carrying out process (a) according to the invention. In this formula (II), R and X preferably represent those radicals which have already been mentioned for these substituents in connection with the description of the substances of the formula (I) according to the invention.

$E^1$ preferably represents halogen, in particular iodine, chlorine or bromine, or represents alkylsulphonyloxy which is optionally substituted by halogen, such as fluorine, chlorine, bromine or iodine, or represents arylsulphonyloxy which is optionally substituted, inter alia, by alkyl having 1 to 4 carbon atoms, such as, for example, methanesulphonyloxy, trifluoromethanesulphonyloxy or p-toluenesulphonyloxy.

The substituted heterocyclic compounds of the formula (II) are new and the invention likewise relates to them. They are obtained by a process in which cyclohexanone derivatives of the formula (V)

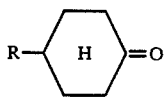 (V)

in which
R has the abovementioned meaning,
are cyclized with alcohols of the formula (VI)

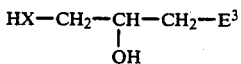 (VI)

in which
X has the abovementioned meaning and
$E^3$ represents halogen or hydroxyl,
is appropriate in the presence of a diluent, such as, for example, toluene, and if appropriate in the presence of an acid catalyst, such as, for example, p-toluenesulphonic acid, at temperatures between 40° C. and 150° C., and, if appropriate, in the cases where $E^3$ in formula (VI) represents a hydroxyl group, the hydroxymethyl-heterocyclic compounds thus obtainable, of the formula (VII)

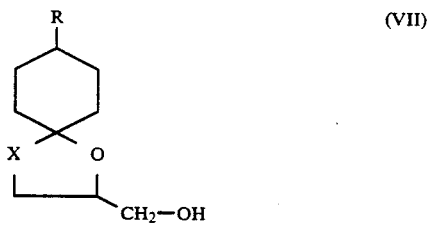

in which
X and R have the abovementioned meanings,
and are reacted in a second stage with optionally substituted alkyl- or arylsulphonyl halides of the formula (VIII)

$$Z-SO_2-Hal \qquad (VIII)$$

in which
Hal represents halogen, in particular chlorine, and
Z represents alkyl which is in each case optionally substituted by halogen, such as fluorine, chlorine, bromine or iodine, or represents aryl which is optionally substituted by alkyl having 1 to 4 carbon atoms, such as, in particular, methyl, trifluoromethyl or 4-methylphenyl,
if appropriate in the presence of a diluent, such as, for example, diethyl ether, and if appropriate in the presence of an acid-binding agent, such as, for example, pyridine or triethylamine, at temperatures between −20° C. and +100° C.

The geometric isomers thereby obtainable can either be further reacted as mixtures in process (a) according to the invention or resolved by customary resolution methods (chromatography or crystallization).

The cyclohexanone derivatives of the formula (V) are known or can be prepared by processes analogous to known processes (compare, for example, Tetrahedron Letters 28, 2347-2350 [1987]; Tetrahedron Lett. 27, 2875-2878 [1986]; Tetrahedron. Lett. 1979, 3209-3212; J. Am. chem. Soc. 109, 6887-6889 [1987]; J.

Am. chem. Soc. 95, 3646-3651 [1973]; J. Am. chem. Soc. 94, 7599-7600 [1972]; Bull. chem. Soc. Jap. 60, 1721-1726 [1987]; Chem. Lett. 1986, 1593-1596; Synth. Commun. 15, 759-764 [1985]; Synth. Commun. 12, 267-277 [1982]; J. chem. Soc. chem. Commun. 1984, 762-763; J. org. Chem. 38, 1775-1776 [1973]; U.S. Pat. No. 4,251,398; U.S. Pat. No. 3,960,961; EP 2,136; DE 2,636,684; DE 2,509,183; FR 2,231,650 and the preparation examples).

The alcohols of the formula (VI) and the sulphonyl halides of the formula (VIII) are generally known compounds of organic chemistry.

Formula (III) provides a general definition of the amines furthermore required as starting substances for carrying out process (a) according to the invention. In this formula (III), $R^1$ and $R^2$ preferably represent those radicals which have already been mentioned for these substituents in connection with the description of the substances of the formula (I) according to the invention.

The amines of the formula (III) are generally known compounds of organic chemistry.

Formula (Ia) provides a general definition of the aminomethylheterocyclic compounds required as starting substances for carrying out process (b) according to the invention. In this formula (Ia), X, R and $R^1$ preferably represent those radicals which have already been mentioned for these substituents in connection with the description of the substances of the formula (I) according to the invention.

The aminomethylheterocyclic compounds of the formula (Ia) are compounds according to the invention and are obtainable with the aid of process (a) according to the invention.

Formula (IV) provides a general definition of the alkylating agents furthermore required as starting substances for carrying out process (b) according to the invention. In this formula (IV), $R^{2-1}$ preferably represents in each case straight-chain or branched alkyl having 1 to 12 carbon atoms, alkenyl having 3 to 8 carbon atoms, alkinyl having 3 to 8 carbon atoms, hydroxyalkyl having 2 to 6 carbon atoms, alkoxyalkyl or dialkoxyalkyl having 1 to 6 carbon atoms or hydroxyalkoxyalkyl having 2 to 6 carbon atoms in the individual alkyl parts, or represents alkoxycarbonylalkyl having 1 to 6 carbon atoms per alkoxy and alkyl part, or represents in each case straight-chain or branched dioxolanylalkyl, dioxanylalkyl or oxolanylalkyl having in each case 1 to 4 carbon atoms in the alkyl part, or represents cycloalkyl or cycloalkylalkyl having in each case 3 to 7 carbon atoms in the cycloalkyl part and if appropriate 1 to 4 carbon atoms in the straight-chain or branched alkyl part and in each case optionally substituted in the cycloalkyl part by one or more identical or different substituents, possible substituents in each case being: halogen and in each case straight-chain or branched alkyl, alkoxy, halogenoalkyl and halogenoalkoxy having in each case 1 to 4 carbon atoms and if appropriate 1 to 9 identical or different halogen atoms; or furthermore represents arylalkyl or arylalkenyl having in each case 6 to 10 carbon atoms in the aryl part and up to 6 carbon atoms in the straight-chain or branched alkyl or alkenyl part and in each case optionally substituted in the aryl part by one or more identical or different substituents, possible substituents on the aryl in each case being: halogen, cyano, nitro and in each case straight-chain or branched alkyl, alkoxy, alkylthio, halogenoalkyl, halogenoalkoxy, halogenoalkylthio, alkoxycarbonyl and alkoximinoalkyl having in each case 1 to 4 carbon atoms in the individual alkyl parts and if appropriate 1 to 9 identical or different halogen atoms.

$R^{2-1}$ particularly preferably represents methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, dioxolanylmethyl, dioxolanylethyl, dioxanylmethyl, dioxanylethyl, oxolanylmethyl or oxolanylethyl, or represents cyclopropyl, cyclopropylmethyl, cyclopropylethyl, cyclopropylpropyl, cyclopentyl, cyclopentylmethyl, cyclohexyl or cyclohexylmethyl, in each case optionally substituted by one to five identical or different substituents from the group comprising fluorine, chlorine, bromine, methyl, ethyl, n- or i-propyl, n-, i-, s- and/or t-butyl, trifluoromethyl or trifluoromethoxy, or represents benzyl or phenethyl, in each case optionally substituted by one to three identical or different substituents, possible substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl and methoximinomethyl.

$R^1$ particularly preferably represents methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, cyclopropylmethyl, oxolanylmethyl, oxolanylethyl, dichlorocyclopropylmethyl, dimethylcyclopropylmethyl, dichlorodimethylcyclopropylmethyl, cyclopentyl, cyclohexyl or cyclohexylmethyl.

$E^2$ preferably represents halogen, in particular chlorine, bromine or iodine, or represents alkylsulphonyloxy or alkoxysulphonyloxy having in each case 1 to 4 carbon atoms and in each case optionally substituted by halogen, such as fluorine, chlorine, bromine or iodine, or represents arylsulphonyloxy which is optionally substituted by, for example, alkyl having 1 to 4 carbon atoms, such as, for example, methanesulphonyloxy, methoxysulphonyloxy or p-toluenesulphonyloxy.

The alkylating agents of the formula (IV) are likewise generally known compounds of organic chemistry or are obtainable by processes analogous to generally known processes.

Possible diluents for carrying out processes (a) and (b) according to the invention are inert organic solvents or aqueous systems. These include, in particular, aliphatic or aromatic optionally halogenated hydrocarbons, such as, for example, benzine, benzene, toluene, xylene, chlorobenzene, petroleum ether, hexane, cyclohexane, methylene chloride, chloroform and carbon tetrachloride, and ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide; esters, such as ethyl acetate; sulphoxides, such as dimethyl sulphoxide, or alcohols, such as methanol, ethanol or propanol.

If appropriate, processes (a) and (b) according to the invention can also be carried out in a two-phase system, such as, for example, water/toluene or water/methylene chloride, if appropriate in the presence of a phase transfer catalyst. Examples which may be mentioned of such catalysts are: tetrabutylammonium iodide, tetrabutylammonium bromide, tributyl-methylphosphonium bromide, trimethyl-$C_{13}$/$C_{15}$-alkylammonium chloride, dibenzyldimethylammonium methyl sulphate, dimethyl-$C_{12}$/$C_{14}$-alkyl-benzylammonium chloride, tetrabutylammonium hydroxide, 15-crown-5, 18-crown-6, triethylbenzylammonium chloride and trimethylbenzylammonium chloride. It is also possible for processes (a) and (b) according to the invention to be carried out without the addition of a solvent.

Possible acid-binding agents for carrying out processes (a) and (b) according to the invention are all the inorganic and organic bases which can usually be employed. Bases which are preferably used are alkali metal hydroxides, alcoholates, carbonates or bicarbonates, such as, for example, sodium hydroxide, sodium methylate, sodium ethylate, sodium carbonate or sodium bicarbonate, and also tertiary amines, such as, for example, triethylamine, N,N-dimethylaniline, pyridine, 4-(N,N-dimethylamino)-pyridine, diazabicyclooctane (DABCO), diazabicyclononen (DBN) or diazabicycloundecene (DBU).

It is also possible for the amines of the formulae (III) or (Ia) used as participants in the reaction to be employed simultaneously in a corresponding excess as the acid-binding agents.

The reaction temperatures can be varied within a substantial range in carrying out processes (a) and (b) according to the invention. The reaction is in general carried out at temperatures between $+20°$ C. and $+200°$ C., preferably at temperatures between $80°$ C. and $+180°$ C.

Processes (a) and (b) according to the invention are in general carried out under normal pressure. However, it is also possible to apply increased pressure in the range between 1 and 10 atmospheres. The procedure under increased pressure is particularly advisable if one or more of the participants in the reaction is in gaseous form under normal pressure at the required reaction temperature.

For carrying out process (a) according to the invention, in general 1.0 to 10.0 mols, preferably 1.0 to 5.0 mols, of amine of the formula (III) and if appropriate 1.0 to 10.0 mols, preferably 1.0 to 5.0 mols of acid-binding agent and if appropriate 0.1 to 1.0 mol of phase transfer catalyst are employed per mol of substituted heterocyclic compound of the formula (II).

For carrying out process (b) according to the invention, in general 1.0 to 5.0 mols, preferably 1.0, to 2.0 mol, of alkylating agent of the formula (IV) and 1.0 to 5.0 mols, preferably 1.0 to 2.0 mols, of acid-binding agent and if appropriate 0.1 to 1.0 mol of phase transfer catalyst are employed per mol of aminomethylheterocyclic compound of the formula (Ia).

In both cases, the reaction is carried out and the reaction products of the formula (I) are worked up and isolated by customary methods.

The acid addition salts, which are tolerated by plants, of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and if appropriate purified by washing with an inert organic solvent.

The active compounds according to the invention exhibit a potent action against pests and can be used in practice for combating undesirable harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilaco nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success here for combating cereal diseases, such as, for example, against the brown glume of wheat causative organism (Leptosphaeria nodorum) or against the leaf spot disease of barley causative organism (*Pyrenophora teres*) or against the leaf spot disease of wheat causative organism (Cochliobolus sativus) and against powdery mildew and rust species, or for combating diseases in fruit and vegetable growing, such as, for example, against the apple scab causative organism (*Venturia inaequalis*) and against Phytophthora and Botrytis species, or for combating diseases in rice growing, such as, for example, against the rice spot disease causative organism (*Pyricularia oryzae*).

The active compounds according to the invention moreover exhibit a good insecticidal activity, for example against leaf aphids (*Myzus persicae*) and plant growth-regulating properties.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or thlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and f synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The active compounds according to the invention can also be used in the preservation of materials for preservation of industrial materials.

According to the invention, industrial materials are non-living materials which have been prepared for use in industry. For example, industrial materials which are to be protected by active compounds according to the invention from microbial change or destruction can be adhesives, sizes, paper and card, textiles, leather, wood, paints and articles made of plastic, cooling lubricants and other materials which can be attacked or decomposed by microorganisms. Components of production lines, for example cooling water circulations, which can be impaired by multiplication of micro-organisms may also be mentioned in the context of materials to be preserved. Adhesives, sizes, paper and card, leather, wood, paints, cooling lubricants and cooling circulations may be mentioned as preferred industrial materials in the context of the present invention.

Examples which may be mentioned of micro-organisms which can cause degradation or a change in industrial materials are bacteria, fungi, yeasts, algae and slime organisms. The active compounds according to the invention preferably act against fungi, in particular molds and wood-discoloring and wood-destroying fungi (Basidiomycetes), and against slime organisms and algae.

Micro-organisms of the following genera may be mentioned as examples:
Alternaria, such as *Alternaria tenuis,*
Aspergillus, such as *Aspergillus niger,*

Chaetomium, such as *Chaetomium globosum*,
Coniophora, such as *Coniophora puteana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeroginosa*, and
Staphylococcus, such as *Staphylococcus aureus*.

An active compound can be converted into the customary formulations according to the field of use, such as solutions, emulsions, suspensions, powders, pastes and granules.

These can be prepared in a manner which is known per se, for example by mixing the active compounds with an extender consisting of a liquid solvent and/or solid carriers, if appropriate using surface-active agents, such as emulsifiers and/or dispersing agents, and if appropriate, in the case where water is used as an extender, organic solvents, such as alcohols, can be used as auxiliaries.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, or halogenated hydrocarbons, such as 1,2-dichloroethane.

Microbicidal agents in general contain the active compounds in an amount of 1 to 95%, preferably 10 to 75%.

The use concentrations of the active compounds according to the invention depend on the nature and occurrence of the micro-organisms to be combated and on the composition of the material to be preserved. The optimum amount to be used can be determined by test series. In general, the use concentrations are in the range from 0.001 to 5% by weight, preferably 0.05 to 1.0% by weight, based on the material to be preserved.

The active compounds according to the invention can also be as a mixture with other known active compounds. The following active compounds may be mentioned as examples: benzyl alcohol mono(poly)hemiformal and other compounds which split off formaldehyde, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzothiazole, organotin compounds, methylenebisthiocyanate and phenol derivatives, such as 2-phenylphenol, (2,2'-dihydroxy-5,5'-dichloro)diphenylmethane and 3-methyl-4-chlorophenol.

PREPARATION EXAMPLES

Example 1

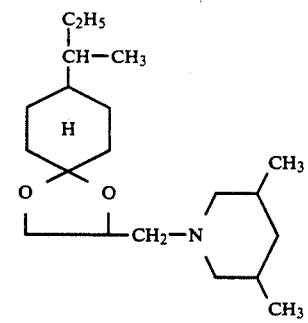 (Process a)

24.7 g (0.1 mol) of 8-s-butyl-2-chloromethyl-1,4-dioxaspiro[4,5]decane and 45.2 g (0.4 mol) of cis-3,5-dimethylpiperidine are stirred at 140° C. for 16 hours and cooled, 200 ml of ethyl acetate are added, the mixture is washed three times with 200 ml of water each time, dried over sodium sulphate and concentrated in vacuo and the residue is purified by chromatography (silica gel; mobile phase: ethyl acetate).

24.3 g (75% of theory) of 8-s-butyl-2-(3,5-dimethylpiperidin-1-ylmethyl)-1,4-dioxaspiro[4,5]decane are obtained as an oil of refractive index $n_D^{20}$ 1.4762

PREPARATION OF THE STARTING COMPOUNDS

Example II-1

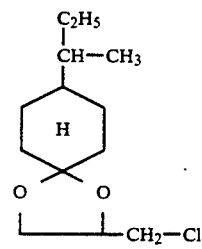

83.7 ml (1 mol) of 3-chloropropane-1,2-diol and, 9:5 g (0.05 mol) of p-toluenesulphonic acid are added to 77 g (0.5 mol) of 4-s-butylcyclohexanone in 1,000 ml of toluene, the mixture is heated under reflux for 16 hours, using a water separator, cooled, washed three times with 1,000 ml of saturated aqueous sodium bicarbonate solution each time, dried over sodium sulphate and concentrated in vacuo and the residue is dried under a high vacuum.

120.4 g (98% of theory) of 8-s-butyl-2-chloromethyl-1,4-dioxaspiro[4,5]decane are obtained as an oil of refractive index $n_C^{20}$ 1.4776.

Example V-a

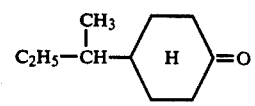

156 g (1 mol) of 4-s-butyl-cyclohexanol are added to a solution of 106.6 g (0.4 mol) of sodium dichromate in 812 ml of water, 92.9 ml of concentrated sulphuric acid are then added dropwise at 70° C., the mixture is allowed to cool to room temperature and is extracted four times with 500 ml of ethyl acetate each time, the combined organic phases are washed twice with 500 ml of 5% strength sodium hydroxide solution each time and once with 500 ml of water and dried over sodium sulphate and the solvent is then removed in vacuo.

131.3 g (85% of theory) of 4-s-butylcyclohexahone of refractive index $n_D^{20}$ 1.3547 are obtained.

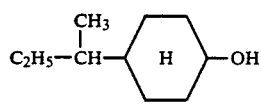

20 g of ruthenium (5% strength on active charcoal) are added to 200 g (1.33 mols)of 4-s-butylphenol (compare, for example, U.S. Pat. No. 3,418,379) in 200 ml of isopropanol and the mixture is hydrogenated in an autoclave at 150° C. under a hydrogen pressure of 200 bar. For working up, the catalyst is filtered off and the solvent is distilled off.

193.4 g (93% of theory) of 4-s-butylcyclohexanol are obtained as an oil of refractive index $n_D^{20}$ 1.4660.

The following aminomethylheterocyclic compounds of the general formula (I) are obtained in a corresponding manner and in accordance with the general instructions for the preparation:

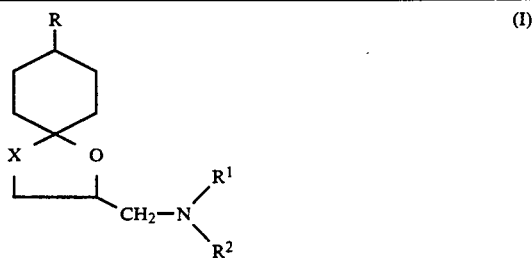

-continued $$\text{(I)}$$

Structure (I): cyclohexane ring with R substituent at position 4, spiro-connected to a 5-membered ring containing X and O, with $-CH_2-N(R^1)(R^2)$ substituent.

| Example No. | X | R | $-N\begin{array}{c}R^1\\R^2\end{array}$ | Physical properties |
|---|---|---|---|---|
| 8 | O | cyclohexyl (H) | piperidino | $n_D^{20}$ 1.4974 |
| 9 | O | cyclohexyl (H) | 3-methylpiperidino | $n_D^{20}$ 1.4935 |
| 10 | O | cyclohexyl (H) | hexamethyleneimino (azepane) | $n_D^{20}$ 1.4997 |
| 11 | O | cyclohexyl (H) | 3,5-dimethylpiperidino | $n_D^{20}$ 1.4909 |
| 12 | O | cyclohexyl (H) | morpholino | $n_D^{20}$ 1.4972 |
| 13 | O | cyclohexyl (H) | 2,6-dimethylmorpholino | $n_D^{20}$ 1.4901 |
| 14 | O | phenyl | $-N(C_2H_5)_2$ | $n_D^{20}$ 1.5113 |
| 15 | O | cyclohexyl (H) | $-N(C_2H_5)_2$ | $n_D^{20}$ 1.4828 |
| 16 | O | cyclohexyl-$CH_2-$ (H) | piperidino | $n_D^{20}$ 1.4969 |

-continued

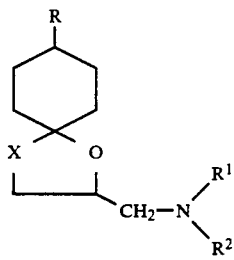

(I)

| Example No. | X | R | $-N\begin{smallmatrix}R^1\\R^2\end{smallmatrix}$ | Physical properties |
|---|---|---|---|---|
| 17 | O | cyclohexyl-CH$_2$— | 3-methylpiperidin-1-yl | $n_D^{20}$ 1.4929 |
| 18 | O | cyclohexyl-CH$_2$— | 3,5-dimethylpiperidin-1-yl (cis) | $n_D^{20}$ 1.4841 |
| 19 | O | cyclohexyl-CH$_2$— | 2,6-dimethylmorpholin-4-yl (cis) | $n_D^{20}$ 1.4868 |
| 20 | O | cyclohexyl-CH$_2$— | 3,5-dimethylpiperidin-1-yl (trans) | $n_D^{20}$ 1.4925 |
| 21 | O | H$_3$C—(CH$_2$)$_2$— | piperidin-1-yl | $n_D^{20}$ 1.4790 |
| 22 | O | H$_3$C—(CH$_2$)$_2$— | 3-methylpiperidin-1-yl | $n_D^{20}$ 1.4764 |
| 23 | O | H$_3$C—(CH$_2$)$_2$— | 2,6-dimethylmorpholin-4-yl (cis) | $n_D^{20}$ 1.4729 |

-continued $$\text{(I)}$$

[Structure I: cyclohexane with R substituent, spiro to dioxolane containing X and O, with CH₂-N(R¹)(R²) side chain]

| Example No. | X | R | -N(R¹)(R²) | Physical properties |
|---|---|---|---|---|
| 24 | O | H₃C—(CH₂)₂— | 3,5-dimethylpiperidin-1-yl | $n_D^{20}$ 1.4746 |
| 25 | O | H₃C—(CH₂)₂— | 3,5-dimethylpiperidin-1-yl | ¹H-NMR*): 3.5–3.68(m, 3H); 4.1–4.3(m, 1H); 4.6–4.75(m, 1H) (salt with saccharin) |
| 26 | O | H₃C—(CH₂)₂— | 3,5-dimethylpiperidin-1-yl | ¹H-NMR*): 3.4–3.9(m, 3H); 4.05–4.2(m, 1H); 4.6–4.75(m, 1H) (salt with p-dodecyl-benzene-sulphonic acid) |
| 27 | O | H₅C₂—CH(CH₃)— | piperidin-1-yl | $n_D^{20}$ 1.4816 |
| 28 | O | H₅C₂—CH(CH₃)— | 3-methylpiperidin-1-yl | $n_D^{20}$ 1.4795 |
| 29 | O | H₅C₂—CH(CH₃)— | hexahydroazepin-1-yl | $n_D^{20}$ 1.4866 |
| 30 | O | H₅C₂—CH(CH₃)— | morpholin-4-yl | $n_D^{20}$ 1.4826 |
| 31 | O | H₅C₂—CH(CH₃)— | cis-3,5-dimethylmorpholin-4-yl | $n_D^{20}$ 1.4775 |

-continued (I)

$$\text{structure with cyclohexane ring bearing R substituent, X, O, and CH}_2\text{-N(R}^1\text{)(R}^2\text{)}$$

| Example No. | X | R | −N(R¹)(R²) | Physical properties |
|---|---|---|---|---|
| 32 | O | cyclohexyl (H) | −NH−C$_2$H$_5$ | n$_D^{20}$ 1.4869 |
| 33 | O | phenyl | −N(CH$_3$)((CH$_2$)$_2$−CH$_3$) | n$_D^{20}$ 1.5110 |
| 34 | O | phenyl | −N(CH$_3$)((CH$_2$)$_3$−CH$_3$) | n$_D^{20}$ 1.5085 |
| 35 | O | phenyl | −N(C$_2$H$_5$)((CH$_2$)$_2$−CH$_3$) | n$_D^{20}$ 1.5086 |
| 36 | O | phenyl | −N(C$_2$H$_5$)((CH$_2$)$_3$−CH$_3$) | n$_D^{20}$ 1.5067 |
| 37 | O | cyclohexyl (H) | −N(C$_2$H$_5$)((CH$_2$)$_2$−CH$_3$) | n$_D^{20}$ 1.4821 |
| 38 | O | cyclohexyl (H) | −N(C$_2$H$_5$)((CH$_2$)$_3$−CH$_3$) | n$_D^{20}$ 1.4825 |
| 39 | O | phenyl | −NH−cyclohexyl(H) | n$_D^{20}$ 1.5254 |
| 40 | O | phenyl | −NH−cyclohexyl(H)(CH$_3$) | n$_D^{20}$ 1.5211 |
| 41 | O | phenyl | −NH−cyclohexyl(H)−CH$_3$ | n$_D^{20}$ 1.5174 |

-continued
$$\text{(I)}$$
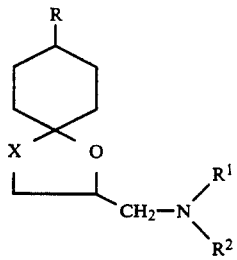
| Example No. | X | R | $-N\begin{matrix}R^1\\R^2\end{matrix}$ | Physical properties |
|---|---|---|---|---|
| 42 | O | 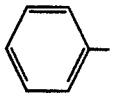 | —NH—(3,5-dimethylphenyl) | ¹H-NMR*⁾: 3.1–3.4(m, 2H); 3.75–3.85(m, 2H) |
| 43 | O | 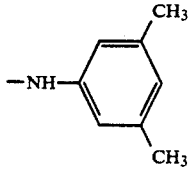 | —NH—(2,4-dimethylphenyl) | ¹H-NMR*⁾: 3.1–3.4(m, 2H); 3.7–3.9(m, 2H); |
| 44 | O |  | —NH—CH(CH₃)—C₆H₅  α(+) | ¹H-NMR*⁾: 3.5–3.9(m, 2H) 3.95–4.05(m, 1H) |
| 45 | O | 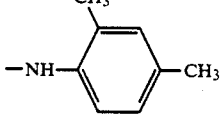 | —NH—CH(CH₃)—C₆H₅  α(−) | ¹H-NMR*⁾: 3.5–3.9(m, 2H); 4.0–4.1(m, 1H) |
| 46 | O |  | —NH—(CH₂)₃—CH₃ | $n_D^{20}$ 1.5145 |
| 47 | O | 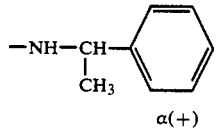 | —N((CH₂)₂—CH₃)((CH₂)₃—CH₃) | $n_D^{20}$ 1.5049 |
| 48 | O |  | —N((CH₂)₃—CH₃)₂ | $n_D^{20}$ 1.5031 |
| 49 | O | 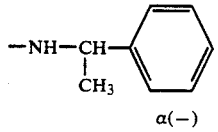 H | —N(3,5-dimethylpiperidinyl) (trans) | ¹H-NMR*⁾: 3.4–3.7(m, 2H); 4.0–4.15(m, 1H) |

-continued (I)

| Example No. | X | R | −N(R¹)(R²) | Physical properties |
|---|---|---|---|---|
| 50 | O | cyclohexyl-H | cis-3,5-dimethylpiperidin-1-yl | ¹H-NMR*): 3.5–3.6(m, 2H); 4.0–4.1(m, 1H) (Diastereomer A) |
| 51 | O | cyclohexyl-H | cis-3,5-dimethylpiperidin-1-yl | ¹H-NMR*): 3.55–3.65(m, 2H); 4.0–4.1(m, 1H) (Diastereomer B) |
| 52 | O | cyclohexyl-H | −NH−(2,5-dimethylcyclohexyl) | ¹H-NMR*): 3.4–3.8(m, 2H); 3.95–4.1(m, 1H) |
| 53 | O | cyclohexyl-H | −NH−(3,5-dimethylcyclohexyl) | ¹H-NMR*): 3.6–3.8(m, 1H) 3.9–4.15(m, 2H) |
| 54 | O | cyclohexyl-H | −N((CH₂)₃−CH₃)₂ | ¹H-NMR*): 3.4–3.7(m, 2H); 3.95–4.1(m, 1H) |
| 55 | O | cyclohexyl-H | −N((CH₂)₂−CH₃)((CH₂)₃−CH₃) | ¹H-NMR*): 3.45–3.7(m, 2H); 3.95–4.1(m, 1H) |
| 56 | O | cyclohexyl-H | cis-2,6-dimethylmorpholin-4-yl | $n_D^{20}$ 1.4909 (Diastereomer A) |
| 57 | O | cyclohexyl-H | cis-2,6-dimethylmorpholin-4-yl | $n_D^{20}$ 1.4884 (Diastereomer B) |

-continued
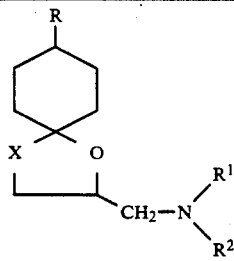 (I)
| Example No. | X | R | −N(R¹)(R²) | Physical properties |
|---|---|---|---|---|
| 58 | O | 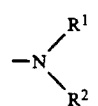 | 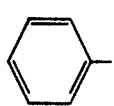 α(+) | $n_D^{20}$ 1.5370 |
| 59 | O | 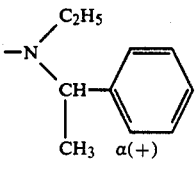 | 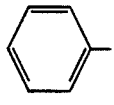 α(−) | $n_D^{20}$ 1.5413 |
| 60 | O | 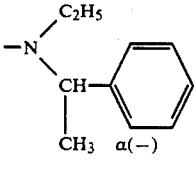 | 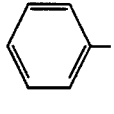 | ¹H-NMR*): 3.65–3.75(m, 1H); 4.0–4.2(m, 2H) |
| 61 | O | 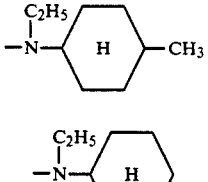 | 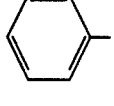 | ¹H-NMR*): 3.65–3.8(m, 1H); 4.0–4.25(m, 2H) |
| 62 | O | 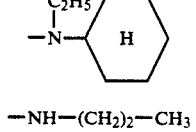 | —NH—(CH₂)₂—CH₃ | bp 120° C./ 0.5 mbar |
| 63 | O | 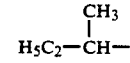 | —NH—(CH₂)₂—OCH₃ | bp 125° C./ 0.5 mbar |
| 64 | O | 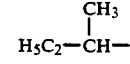 | 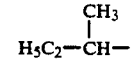 | $n_D20$ 1.4837 |
| 65 | O | 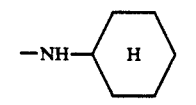 | 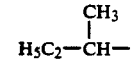 | $n_D20$ 1.4805 |
| 66 | O | 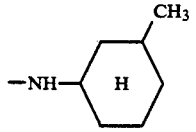 | 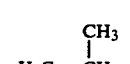 | $n_D20$ 1.4851 |
| 67 | O | 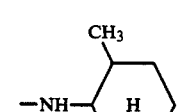 | 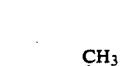 | $n_D20$ 1.4793 |

-continued (I)

| Example No. | X | R | $-N\begin{smallmatrix}R^1\\R^2\end{smallmatrix}$ | Physical properties |
|---|---|---|---|---|
| 68 | O | H₅C₂—CH— with CH₃ | —NH—CH₂—(cyclohexyl with H) | $n_D 20$ 1.4797 |
| 69 | S | phenyl | piperidin-1-yl | mp: 29–31° C. |
| 70 | S | phenyl | 3,5-dimethylpiperidin-1-yl (cis) | mp: 34–36° C. |
| 71 | S | phenyl | 2,6-dimethylmorpholin-4-yl (cis) | mp: 38° C. |
| 72 | S | phenyl | —NH—CH₂—(cyclohexyl H) | $n_D^{20}$ 1.5462 |
| 73 | S | phenyl | —NH—CH₂—(tetrahydrofuran-2-yl) | $n_D^{20}$ 1.5514 |
| 74 | S | phenyl | —N(CH₂)₂—CH₃ / —CH₂—(tetrahydrofuran-2-yl) | $n_D^{20}$ 1.5364 |
| 75 | S | phenyl | —NH—(CH₂)₃—OC₂H₅ | $n_D^{20}$ 1.5329 |
| 76 | S | phenyl | —NH—CH₂—(cyclohexyl H) | $n_D^{20}$ 1.5591 (salt with saccharin) |

-continued $$\text{(I)}$$

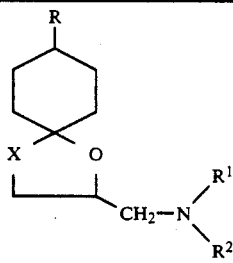

| Example No. | X | R | $-N\begin{smallmatrix}R^1\\R^2\end{smallmatrix}$ | Physical properties |
|---|---|---|---|---|
| 77 | S | phenyl | −NH−CH₂−(tetrahydrofuran-2-yl) | $n_D^{20}$ 1.5600 (salt with saccharin) |
| 78 | S | phenyl | 3,5-dimethylpiperidin-1-yl (cis) | $n_D^{20}$ 1.5452 (salt with saccharin) |
| 79 | S | phenyl | 2,6-dimethylmorpholin-4-yl (cis) | $n_D^{20}$ 1.5509 (salt with saccharin) |
| 80 | S | phenyl | −N(CH₂−C≡CH)−CH₂−(tetrahydrofuran-2-yl) | $n_D^{20}$ 1.5539 |
| 81 | S | phenyl | −N(CH₂−C≡CH)((CH₂)₃−OC₂H₅) | $n_D^{20}$ 1.5440 |
| 82 | S | phenyl | morpholin-4-yl | $n_D^{20}$ 1.5538 |
| 83 | S | phenyl | 3-methylpiperidin-1-yl | ¹H-NMR*): 4.3–4.55(m, 1H) 3.0–3.2(m, 2H) |
| 84 | S | phenyl | hexamethyleneimin-1-yl | 4.25–4.5(m, 1H) 3.05–3.15(m, 1H) 2.6–3.0(m, 7H) |
| 85 | S | phenyl | −NH−(3-methylcyclohexyl) | $n_D^{20}$ 1.5346 |

-continued (I)

| Example No. | X | R | −N(R¹)(R²) | Physical properties |
|---|---|---|---|---|
| 86 | S | phenyl | −NH−CH₂−CH(CH₃)₂ | $n_D^{20}$ 1.5269 |
| 87 | S | phenyl | −NH−CH₂−CH(C₂H₅)₂ | $n_D^{20}$ 1.5074 |
| 88 | S | phenyl | morpholino | ¹H-NMR*): 4.65–4.9(m, 1H) 3.9–4.15(m, 4H) 3.05–3.65(m, 4H) (salt with saccharin) |
| 89 | S | cyclohexyl (H) | 2,6-dimethylmorpholino | $n_D^{20}$ 1.5141 |
| 90 | S | cyclohexyl (H) | 3,5-dimethylpiperidino | $n_D^{20}$ 1.4990 |
| 91 | S | cyclohexyl (H) | −NH−(3-methylcyclohexyl) | $n_D^{20}$ 1.5232 |
| 92 | S | cyclohexyl (H) | −NH−(CH₂)₂−OCH₃ | $n_D^{20}$ 1.5948 |
| 93 | S | cyclohexyl (H) | −N((CH₂)₂−CH₃)((CH₂)₂−OCH₃) | $n_D^{20}$ 1.5068 |
| 94 | O | −CH(CH₃)C₂H₅ | −N(C₂H₅)((CH₂)₂CH₃) | $n_D^{20}$ 1.4635 |

-continued $$\text{(I)}$$

[Structure: cyclohexane ring with R substituent, containing X and O with CH₂—N(R¹)(R²) group]

| Example No. | X | R | —N⟨R¹/R² | Physical properties |
|---|---|---|---|---|
| 95 | O | —CH(CH₃)C₂H₅ | —N⟨C₂H₅ / (CH₂)₃CH₃ | $n_D^{20}$ 1.4640 |
| 96 | O | —CH(CH₃)C₂H₅ | —N⟨C₂H₅ / (CH₂)₂OCH₃ | $n_D^{20}$ 1.4640 |
| 97 | O | —CH(CH₃)C₂H₅ | —N⟨C₃H₇ / (CH₂)₂OCH₃ | $n_D^{20}$ 1.4619 |
| 98 | O | —CH(CH₃)C₂H₅ | —N⟨CH₃ / C₂H₅ | $n_D^{20}$ 1.4633 |
| 99 | O | —CH(CH₃)C₂H₅ | —N⟨CH₃ / (CH₂)₂CH₃ | $n_D^{20}$ 1.4629 |
| 100 | O | —CH(CH₃)C₂H₅ | —N⟨CH₃ / (CH₂)₃CH₃ | $n_D^{20}$ 1.4635 |
| 101 | O | —CH(CH₃)C₂H₅ | —N⟨(CH₂)₂CH₃ / (CH₂)₂CH₃ | $n_D^{20}$ 1.4645 |
| 102 | O | —CH(CH₃)C₂H₅ | —N⟨(CH₂)₂CH₃ / (CH₂)₃CH₃ | $n_D^{20}$ 1.4637 |
| 103 | O | —CH₂-cyclohexyl(H) | —N⟨CH₃ / C₂H₅ | $n_D^{20}$ 1.4794 |
| 104 | O | —CH₂-cyclohexyl(H) | —N⟨CH₃ / (CH₂)₂CH₃ | $n_D^{20}$ 1.4789 |
| 105 | O | —CH₂-cyclohexyl(H) | —N⟨CH₃ / (CH₂)₃CH₃ | $n_D^{20}$ 1.4775 |

-continued

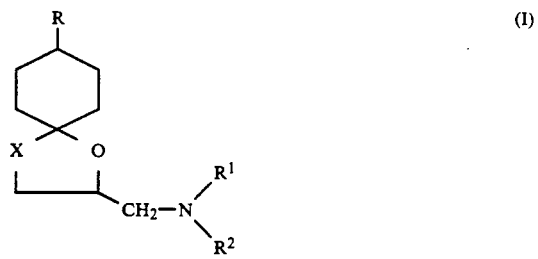 (I)

| Example No. | X | R | −N(R¹)(R²) | Physical properties |
|---|---|---|---|---|
| 106 | O | −CH₂−C₆H₁₁ (cyclohexyl, H) | −N(C₂H₅)((CH₂)₂OCH₃) | $n_D^{20}$ 1.4772 |
| 107 | O | −CH₂−C₆H₁₁ (cyclohexyl, H) | −N((CH₂)₃CH₃)((CH₂)₂OCH₃) | $n_D^{20}$ 1.4757 |
| 108 | O | −CH(CH₃)C₃H₇ | piperidin-1-yl | $n_D^{20}$ 1.4816 |
| 109 | O | −CH(CH₃)C₃H₇ | 3-methylpiperidin-1-yl | $n_D^{20}$ 1.4821 |
| 110 | O | −CH(CH₃)C₃H₇ | 3,5-dimethylpiperidin-1-yl | $n_D^{20}$ 1.4782 |
| 111 | O | −CH(CH₃)C₃H₇ | 2,6-dimethylmorpholin-4-yl | $n_D^{20}$ 1.4757 |
| 112 | O | −CH(C₂H₅)C₂H₅ | piperidin-1-yl | $n_D^{20}$ 1.4832 |
| 113 | O | −CH(C₂H₅)C₂H₅ | 3-methylpiperidin-1-yl | $n_D^{20}$ 1.4810 |

-continued

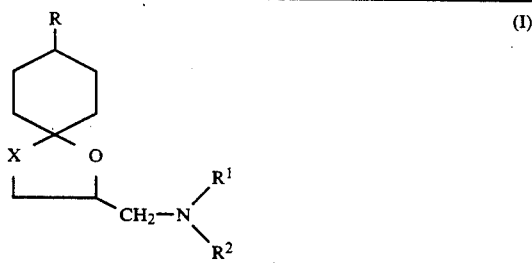
(I)

| Example No. | X | R | $-N\begin{matrix}R^1\\R^2\end{matrix}$ | Physical properties |
|---|---|---|---|---|
| 114 | O | —CH(C₂H₅)C₂H₅ | 3,5-dimethylpiperidin-1-yl | $n_D^{20}$ 1.4792 |
| 115 | O | —CH(C₂H₅)C₂H₅ | 2,6-dimethylmorpholin-4-yl | $n_D^{20}$ 1.4766 |
| 116 | O | —CH(C₂H₅)C₂H₅ | —NH—cyclohexyl | $n_D^{20}$ 1.4863 |
| 117 | O | —CH(C₂H₅)C₂H₅ | —N(CH₃)—cyclohexyl | $n_D^{20}$ 1.4857 |
| 118 | O | —CH(C₂H₅)C₂H₅ | —NH—(3-methylcyclohexyl) | $n_D^{20}$ 1.4825 |
| 119 | O | —CH(CH₃)CH₂CH(CH₃)₂ | 3-methylpiperidin-1-yl | $n_D^{20}$ 1.4799 |
| 120 | O | —CH(CH₃)CH₂CH(CH₃)₂ | 3,5-dimethylpiperidin-1-yl | $n_D^{20}$ 1.4769 |
| 121 | O | —CH(CH₃)C₅H₁₁ | —N(CH₃)—cyclohexyl | $n_D^{20}$ 1.3890 |

-continued $$\text{(I)}$$

[Structure: cyclohexane with R substituent at top, spiro-fused to a 1,3-dioxolane-type ring containing X and O, with a CH₂-N(R¹)(R²) substituent]

| Example No. | X | R | −N(R¹)(R²) | Physical properties |
|---|---|---|---|---|
| 122 | O | −CH(CH₃)C₅H₁₁ | −N(piperidinyl) | $n_D^{20}$ 1.4808 |
| 123 | O | −CH(CH₃)C₅H₁₁ | −N(3-methylpiperidinyl) | $n_D^{20}$ 1.4805 |
| 124 | O | −CH(C₂H₅)C₂H₅ | −NH−(CH₂)₂OCH₃ | $n_D^{20}$ 1.4707 |
| 125 | O | −CH(C₂H₅)C₂H₅ | −NH−(CH₂)₂CH₃ | $n_D^{20}$ 1.4687 |
| 126 | O | −CH(CH₃)CH₂CH(CH₃)₂ | −NH−(CH₂)₂CH₃ | $n_D^{20}$ 1.4659 |
| 127 | O | −CH(CH₃)C₅H₁₁ | −N(3,5-dimethylpiperidinyl) | $n_D^{20}$ 1.4767 |
| 128 | O | −CH(CH₃)C₅H₁₁ | −N(2,6-dimethylmorpholinyl) | $n_D^{20}$ 1.4759 |
| 129 | O | −CH(CH₃)C₅H₁₁ | −NH−cyclohexyl | $n_D^{20}$ 1.4855 |
| 130 | O | −CH(CH₃)C₅H₁₁ | −NH−(3-methylcyclohexyl) | $n_D^{20}$ 1.4813 |
| 131 | O | −CH(CH₃)C₅H₁₁ | −NH−C₂H₅ | $n_D^{20}$ 1.4525 |
| 132 | O | −CH(CH₃)C₅H₁₁ | −NH−(CH₂)₂CH₃ | $n_D^{20}$ 1.4669 |
| 133 | O | −CH(C₂H₅)C₂H₅ | −N((CH₂)₂OCH₃)((CH₂)₂CH₃) | $n_D^{20}$ 1.4623 |
| 134 | O | −CH(C₂H₅)C₂H₅ | −N((CH₂)₂CH₃)₂ | $n_D^{20}$ 1.4636 |

-continued $$\text{(I)}$$

Structure: cyclohexane with R substituent at top, spiro-fused to a 1,3-dioxolane-type ring (X—CH₂—CH(—CH₂—N(R¹)(R²))—O—), where X and O are attached to the spiro carbon.

| Example No. | X | R | —N(R¹)(R²) | Physical properties |
|---|---|---|---|---|
| 135 | O | —CH(CH₃)CH₂CH(CH₃)₂ | —N((CH₂)₂CH₃)((CH₂)₂CH₃) | $n_D^{20}$ 1.4642 |
| 136 | O | —CH(C₂H₅)C₂H₅ | —N(C₂H₅)((CH₂)₂CH₃) | $n_D^{20}$ 1.4675 |
| 137 | O | —CH(C₂H₅)C₂H₅ | —N(C₂H₅)((CH₂)₃CH₃) | $n_D^{20}$ 1.4670 |
| 138 | O | —CH(CH₃)C₃H₇ | —N(CH₃)(cyclohexyl-H) | $n_D^{20}$ 1.4869 |
| 139 | O | —CH(CH₃)C₃H₇ | —NH—(cyclohexyl-H) | $n_D^{20}$ 1.4817 |
| 140 | O | —CH(CH₃)C₃H₇ | —NH—(3-methylcyclohexyl-H) | $n_D^{20}$ 1.4834 |
| 141 | O | —CH(CH₃)C₃H₇ | —NH—C₂H₅ | $n_D^{20}$ 1.4657 |
| 142 | O | —CH(CH₃)C₃H₇ | —NH—(CH₂)₂OCH₃ | $n_D^{20}$ 1.4677 |
| 143 | O | —CH(CH₃)C₃H₇ | —NH—(CH₂)₂CH₃ | $n_D^{20}$ 1.4674 |
| 144 | O | —CH(CH₃)C₃H₇ | —N((CH₂)₂CH₃)((CH₂)₂CH₃) | $n_D^{20}$ 1.4653 |
| 145 | O | —CH(CH₃)C₃H₇ | —N((CH₂)₂CH₃)((CH₂)₂OCH₃) | $n_D^{20}$ 1.4647 |
| 146 | O | —CH(CH₃)C₃H₇ | —N(C₂H₅)((CH₂)₂CH₃) | $n_D^{20}$ 1.4633 |
| 147 | O | —CH(CH₃)C₅H₁₁ | —N((CH₂)₂CH₃)((CH₂)₂OCH₃) | $n_D^{20}$ 1.4657 |

-continued

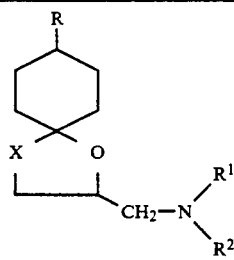
(I)

| Example No. | X | R | −N(R¹)(R²) | Physical properties |
|---|---|---|---|---|
| 148 | O | −CH(CH₃)C₃H₇ | −N(C₂H₅)((CH₂)₃CH₃) | $n_D^{20}$ 1.4652 |
| 149 | O | −CH(CH₃)C₅H₁₁ | −N((CH₂)₂CH₃)₂ | $n_D^{20}$ 1.4644 |
| 150 | O | −CH(CH₃)C₅H₁₁ | −N(C₂H₅)((CH₂)₂CH₃) | $n_D^{20}$ 1.4641 |
| 151 | O | −CH(CH₃)C₅H₁₁ | −N(C₂H₅)((CH₂)₃CH₃) | $n_D^{20}$ 1.4655 |
| 152 | O | cyclohexyl-H | −NH−(4-CF₃-cyclohexyl) | Oil |
| 153 | O | cyclohexyl-H | −NH−(3,5-bis-CF₃-cyclohexyl) | Oil |
| 154 | O | cyclohexyl-H | −NH−(4-CF₃-cyclohexyl) | Oil (diastereom. A) |
| 155 | O | −CH(C₃H₇)₂ | −N(piperidine) | $n_D^{20}$ 1.4814 |
| 156 | O | −CH(C₃H₇)₂ | −N(CH₃)(cyclohexyl) | $n_D^{20}$ 1.4846 |
| 157 | O | −CH(C₃H₇)₂ | −NH−C₃H₇ | $n_D^{20}$ 1.4664 |
| 158 | O | −CH(C₃H₇)₂ | −NH−(CH₂)₂OCH₃ | $n_D^{20}$ 1.4659 |
| 159 | O | −CH(C₃H₅)₂ | −NH−C₅H₁₁ | $n_D^{20}$ 1.4689 |

-continued $$\text{(I)}$$

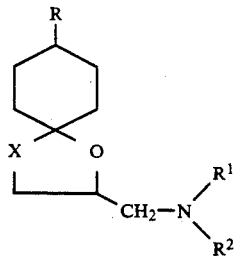

| Example No. | X | R | $-N\begin{matrix}R^1\\R^2\end{matrix}$ | Physical properties |
|---|---|---|---|---|
| 160 | O | $-CH(C_3H_7)_2$ | 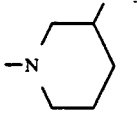 | $n_D^{20}$ 1.4786 |
| 161 | O | $-CH(C_3H_7)_2$ | 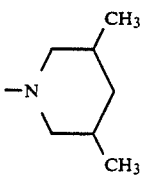 | $n_D^{20}$ 1.4773 |
| 162 | O | $-CH(C_3H_7)_2$ | 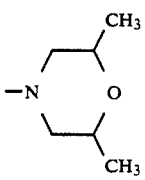 | $n_D^{20}$ 1.4768 |
| 163 | O | $-CH(C_3H_7)_2$ | 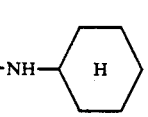 | $n_D^{20}$ 1.4854 |
| 164 | O | $-CH(C_3H_7)_2$ | 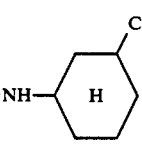 | $n_D^{20}$ 1.4814 |

USE EXAMPLES

The compounds shown below were employed as comparison substances in the use examples which follow:

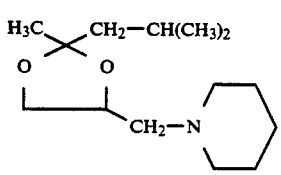

2-isobutyl-2-methyl-4-(1-piperidinylmethyl)-1,3-dioxolane (A)

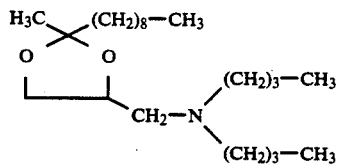

2-Methyl-2-nonyl-4-di-n-butylaminomethyl-1,3-dioxolane (B)

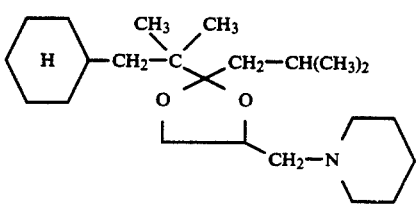

2-(2-Cyclohexylmethyl-2-propyl)-2-methyl-4-(1-piperidinyl- (C)

-continued
methyl)-1,3-dioxolane

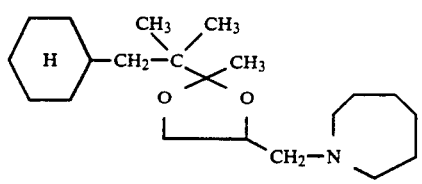

2-(2-cyclohexylmethyl-2-propyl)-2-methyl-4-(1-perhydro-azepinylmethyl)-1,3-dioxolane (all known from EP 97,822).

EXAMPLE A

*Leptosphaeria nodorum* Test (Wheat)/Protective/

Solvent 100 parts by weight of dimethylformamide
Emulsifier: 0.25 parts by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, for example, a clearly superior activity compared with the prior art is shown, for example, by the compounds according to Preparation Examples 3, 8, 9, 10, 14, 26, 27, 28, 29, 39, 40, 41, 44, 45, 46, 47, 48, 52, 55, 70, 72, 75 and 85.

EXAMPLE B

*Cochliobolus sativus* Test (Barley)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Cochliobolus sativus. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, for example, a clearly superior activity compared with the prior art is shown, for example, by the compounds according to Preparation Examples 39, 40, 41, 42, 44, 45, 55, 72, 75 and 85.

EXAMPLE C

Venturia Test (Apple)/Protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples 40 and 41.

EXAMPLE D

The compounds according to the invention were incorporated in graduated concentrations of between 1 and 5,000 mg/l of test samples into an agar prepared from beer wort and peptone. After the agar had solidified, the agar samples thus prepared were contaminated with pure cultures of various test fungi.

After storage at 28° C. and 60 to 70% relative atmospheric humidity for two weeks, the experiment was evaluated. The minimum concentration of substance contained in an agar sample at which no growth at all of the species used took place is stated as the minimum inhibitory concentration (MIC) in the table.

In this test, for example, compounds 52, 53, 15, 9 and 10 exhibit a very good action.

It will be understood that the specification and examples are illustrative but not limitative of the present invention and that other embodiments within the spirit and scope of the invention will suggest themselves to those skilled in the art.

We claim:

1. An aminomethylheterocyclic compound of the formula

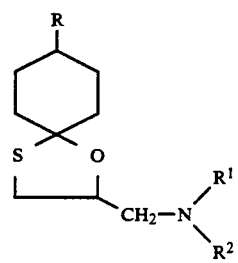

wherein

R represents cycloalkyl having 3 to 7 carbon atoms, or represents aryl which has 6 to 10 carbon atoms and is optionally substituted by one or more identical or different straight-chain or branched alkyl radicals having 1 to 12 carbon atoms, $R^1$ and $R^2$ independently of one another each represent hydrogen, or represent straight-chain or branched alkyl having 1 to 12 carbon atoms, alkenyl having 3 to 8 carbon atoms, alkynyl having 3 to 8 carbon atoms, hydroxyalkyl having 2 to 6 carbon atoms, alkoxyalkyl or dialkoxyalkyl having in each case 1 to 6 carbon atoms or hydroxyalkoxyalkyl having 2 to 6 carbon atoms in the individual alkyl parts, or represent alkoxycarbonylalkyl having 1 to 6 carbon atoms per alkoxy and alkyl part, or represent straight-chain or branched dioxolanylalkyl, dioxanylalkyl or oxolanylalkyl having in each case 1 to 4 carbon atoms in the alkyl part, or represent cycloalkyl or cycloalkylalkyl having 3 to 7 carbon atoms in the cycloalkyl part and if appropriate 1 to 4 carbon atoms in the straight-chain or branched alkyl part and optionally substituted in the cycloalkyl part by one or more identical or different substituents selected from the group consisting of halogen, and straight-chain or branched alkyl, alkoxy, halogenolalkyl and halogenoalkoxy having 1 to 4 carbon atoms and if appropriate 1 to 9 identical or different halogen atoms; or in addition represent arylalkyl, arylalkenyl or aryl having 6 to 10 carbon atoms in the aryl part and if appropriate up to 6 carbon atoms in the straight-chain or branched alkyl or alkenyl part and optionally substituted in the aryl part by one or more identical or different substituents selected from the group consisting of halogen, cyano, nitro, and straight-chain or branched alkyl, alkoxy, alkylthio, halogenoalkyl, halogenoalkoxy, halogenoalkylthio, alkoxycarbonyl and alkoximinoalkyl having 1 to 4 carbon atoms in the individual alkyl parts and if appropriate 1 to 9 identical or different halogen atoms, or an acid salt addition thereof.

2. An aminomethylheterocyclic compound or salt thereof according to claim 1,
wherein
R represents cyclopentyl or cyclohexyl, or represents phenyl which is optionally substituted by one to three identical or different substituents from the group consisting of methyl, ethyl, n- or i-propyl and n-, i-, s- or t-butyl, $R^1$ and $R^2$ independently of one another each represent hydrogen methyl, ethyl, n- or i-propyl, n-, i-, s- or t-butyl, n- or i-pentyl, n- or i-hexyl, n-butenyl, n- or i-pentenyl, propargyl,, n- or i-butynyl, hydroxyethyl, hydroxypropyl, methoxyethyl, ethoxyethyl, propoxyethyl, butoxyethyl, methoxoypropyl, ethoxypropyl, propoxypropyl, butoxypropyl, hydroxyethoxyethyl, dimethoxyethyl, dimethoxypropyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, or represent cyclopropyl, cyclopropylmethyl, cyclopropylethyl, cyclopropylpropyl, cyclopentyl, cyclopentylmethyl, cyclohexyl or cyclohexylmethyl, optionally substituted by one to five identical or different substituents from the group fluorine, chlorine, bromine, methyl, ethyl, n- or i-propyl, n-, i-, s- or t-butyl, trifluoromethyl and trifluoromethoxy, or represent phyenyl, benzyl or phenethyl, optionally substituted by one to three identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl and methoximinomethyl.

3. An aminomethylheterocyclic compound or salt thereof according to claim 1,
wherein
R represents cyclohexyl, or represents phenyl, $R^1$ and $R^2$ independently of one another each represent hydrogen, methyl, ethyl, n- or i-propyl, n-, i-, s- or t-butyl, n- or i-pentyl, n- or i-hexyl, allyl, n- or i-butenyl, n- or i-pentenyl, propargyl, n- or i-butynyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, cyclopropylmethyl, dichlorocyclopropylmethyl, dimethylcyclopropylmethyl, dichlorodimethylcyclypropylmethyl, cyclopentyl, cyclohexyl or cyclohexylmethyl.

4. A fungicidal composition comprising a fungicidally effective amount of a compound or salt thereof according to claim 1 and a diluent.

5. A method Of combating fungi which comprises applying to such fungi or to a fungus habitat a fungicidally effective amount of a compound or salt thereof according to claim 1.

* * * * *